United States Patent [19]

Yogosawa

[11] 4,137,443
[45] Jan. 30, 1979

[54] WELDING APPARATUS FOR DENTAL PURPOSES

[75] Inventor: Fumio Yogosawa, Tokyo, Japan

[73] Assignee: Sankin Kogyo, Ltd., Osaka, Japan

[21] Appl. No.: 789,092

[22] Filed: Apr. 20, 1977

[30] Foreign Application Priority Data

Nov. 11, 1976 [JP] Japan .................................. 51-151415

[51] Int. Cl.² ............................................. B23K 11/28
[52] U.S. Cl. ................................. 219/86.21; 219/86.25
[58] Field of Search ............... 219/108, 109, 111, 112, 219/113, 78.01, 86.21, 86.25, 86.31, 86.33, 86.41

[56] References Cited

U.S. PATENT DOCUMENTS

| 2,772,345 | 11/1956 | Gainsforth | 219/86.21 |
| 3,127,501 | 3/1964 | Mueller | 219/86.33 |
| 3,307,012 | 2/1967 | Ryan et al. | 219/86.21 |

Primary Examiner—J. V. Truhe
Assistant Examiner—Clifford C. Shaw
Attorney, Agent, or Firm—Eliot S. Gerber

[57] ABSTRACT

An improved welding apparatus for dental purposes which allows a welding operation while materials to be welded are supported in position by hands. In the apparatus, an welding current is applied to electrodes of the apparatus by merely pushing a plate while keeping the materials to be welded in position between the electrodes.

6 Claims, 7 Drawing Figures

WELDING APPARATUS FOR DENTAL PURPOSES

BRIEF SUMMARY OF THE INVENTION

The present invention relates to a welding apparatus used for dental purposes, and more particularly to an orthodontic welding apparatus of condenser-welding system, which allows a spot welding or resistance welding.

According to conventional welding apparatus for orthodontic purposes, which are generally of hand-carrying or portable type, a main ON-OFF switch for supplying an electric current for welding to electrodes have been provided on the side of the apparatus. In a welding operation of the conventional apparatus, the main switch is put on in the first place, and articles or materials to be welded together are then inserted in position and held between the upper and lower electrodes with a suitable pressure of a spring and the like. After the materials are snugly held by the two electrodes, the separate welding switch is put on by hand to supply a welding current to the electrodes. After the welding is founded to be complete and desirable, the welding switch is put off by hand.

However, it has been quite difficult to operate the welding switch while keeping the materials in position by hands. The materials to be welded together in the orthodontic field are quite small sized, and therefore the materials should be supported or kept in position by hands while the materials are held between the electrodes. Otherwise, it has been found that the materials to be welded together, which were once held in position between the electrodes, were slipped off and got out of position, and failed a desired spot welding. Furthermore, it has been awkwardly troublesome to release one of the hands, which grasp a pinsette or pinsettes to secure the materials, and then to operate the welding switch.

Accordingly, an object of the present invention is to provide an improved welding apparatus for orthodontic purposes, which allows an easy switching operation while materials to be welded together are maintained in position by hands.

Another object of the present invention is to provide an improved welding apparatus for orthodontic purposes, which allows a reliable welding by a single manual operation.

Further object of the present invention is to provide an improved welding apparatus for orthodontic purposes, which allows a continued operation of securing in position the materials to be welded and of feeding an electric currency to electrodes of the apparatus.

Other object and features of the present invention will become apparent from the detailed description of the preferred embodiment thereof, which will be read with the accompanying drawings.

DETAILED DESCRIPTION OF THE INVENTION

Figure 1:
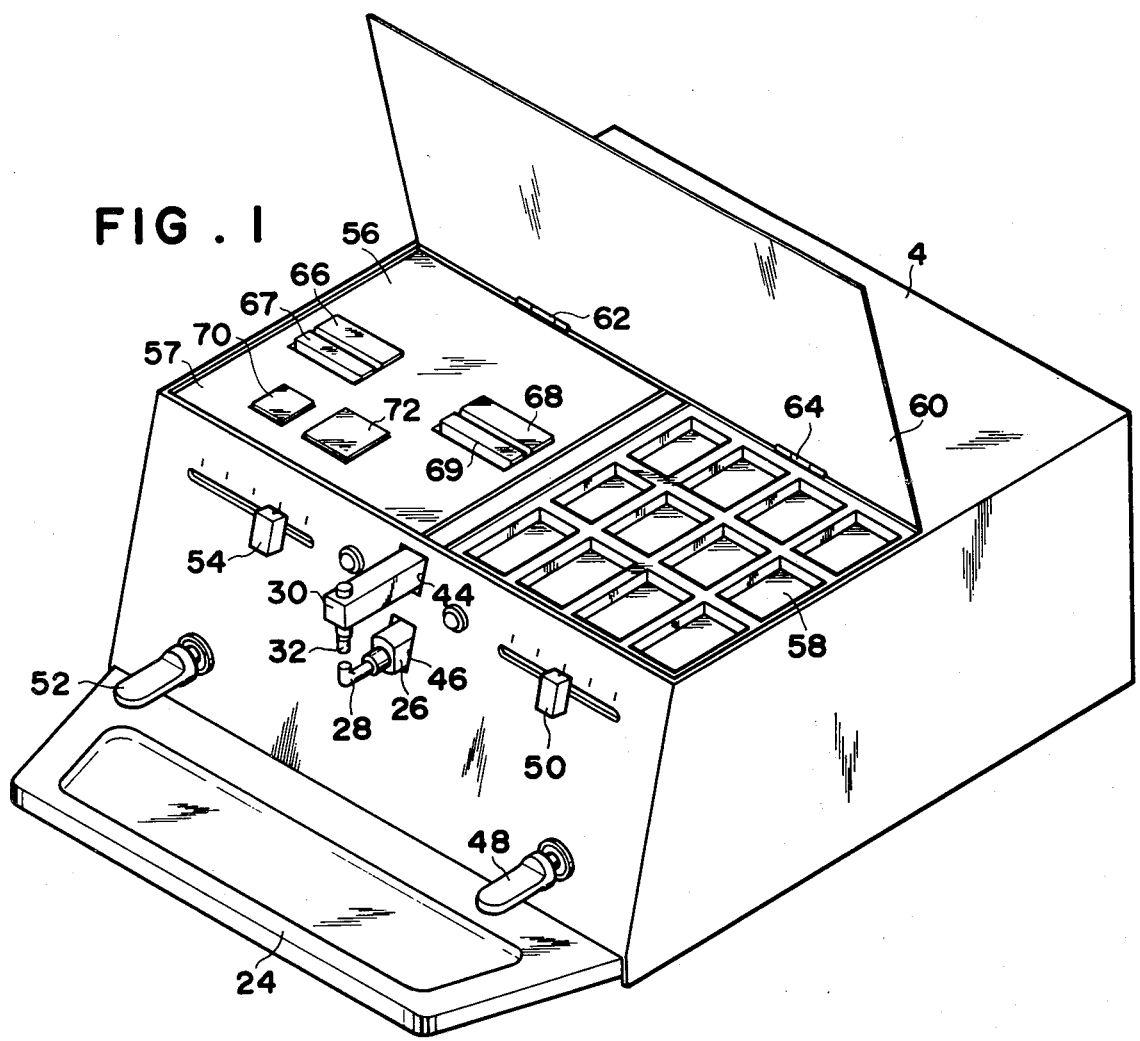
FIG. 1 is a perspective view of an orthodontic welding apparatus embodying the present invention.

In FIGS. 1, 2, 3A and 3B, a plastic box-shaped structure is formed with a rectangular base plate 2 and a casing 4. The cover 4 is removably connected to the base plate 2. On the base plate 2 are disposed a mechanism 6 for supporting electrodes, which will be discribed below, and an electric circuit devices 8 which will be described below.

The supporting mechanism 6 comprises two legs 10 and 12, each of which is fixed at its lower end to the base plate 2 with a predetermined space between the legs 10 and 12. A cylindrical or round shaped bar 14, which is made of a suitable material such as steel or plastics, is fixed to the upper end portion of the legs 10 and 12. Adjacent to the connection points of the legs and the bar, there are disposed "L" shaped arms 16 and 18, which have a hole and are swingably contacted with the bar 14. The arms 16 and 18 are fixed to a plate 20 of plastics such that the plate 20 is swingable about the bar 14. The plate 20 has a width slightly smaller than the distance between the legs 10 and 12, and an aperture 22 of rectangular shape. The lower extremity of the plate 22 is fixed to a switching board 24 which has an extension 24' as well shown in FIG. 2. Namely, the extension 24' of the switching board 24 is overlapped with a slight space above a front portion of the base 2 and connected to the plate 20 which is vertically and swingably supported by means of the legs 10, 12, bar 14 and arms 16, 18. The switching board 24 is preferably made integral with the plate 20, as well illustrated in FIGS. 3A and 3B.

At the middle of the bar 14 is disposed a holder 26 of "L" shape, which is swingable about, but not slidable in the lengthwise direction of, the bar 14. The holder 26 has, at its one end, a removable lower electrode 28 which is "anvil" shaped, and is extended toward the front of the apparatus through the aperture 22 of the plate 20. An upper holder 30 is connected at its one end to the upper portion of the plate 20 such that the upper holder 30 is substantially parallel with the holder 26 of the lower electrode 26. An upper electrode 32 is removably disposed at the other end of the upper holder 30 such that opposed surfaces, or points, of the upper and lower electrodes 28 and 32 will be in tight facewise, or pointwise, abutment in operation. Namely, the upper electrode 32 is always moved downwardly against the tip of the lower electrode 28 in exact abutment without danger of canting. Though the plate 20 is illustrated such that the same has a step and is staired at its upper portion, it should be understood that the plate 20 may be of plain, flat shape.

At rear of the holder 26, a switching device 34 is provided on the base 2. The switching device 34 has a microswitch, which is well known in the art and therefore a detailed description thereof will not be made. The microswitch of the switching device has an actuator 36, which extends and slightly contacts the lower portion of the lower holder 26.

Figure 3A:
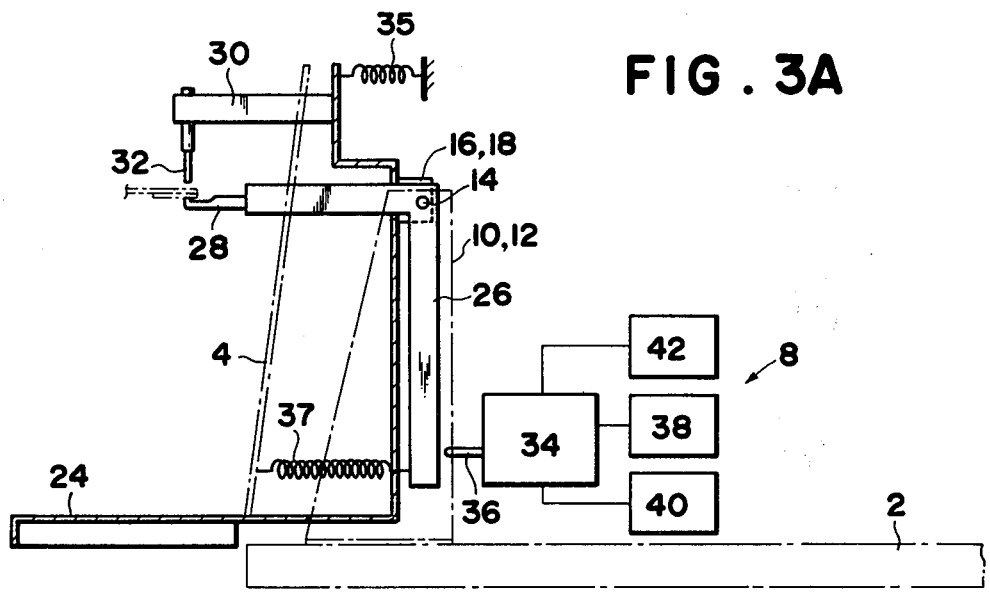
FIGS. 3A and 3B are side views, diagrammatically showing an operation of the principal mechanism of the orthodontic welding apparatus.
Figure 3B:
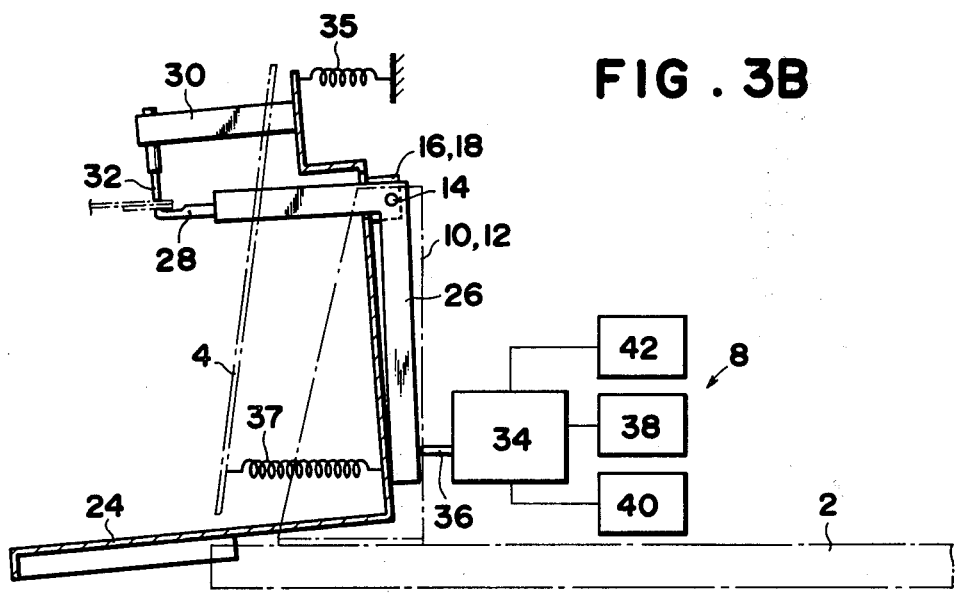

As shown in FIGS. 3A and 3B, the upper and lower holders 30 and 26 are generally kept parallel to each other by means of springs 35 and 37, respectively. One end of the springs 35 and 37 is connected to a suitable position of the casing 4.

Figure 4:
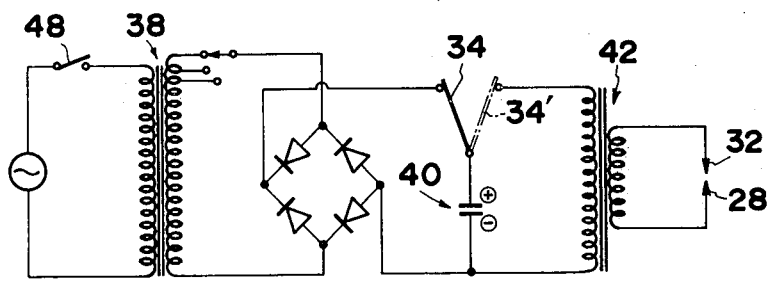
FIG. 4 is a circuit diagram used in the orthodontic welding apparatus of the present invention.
Figure 2:
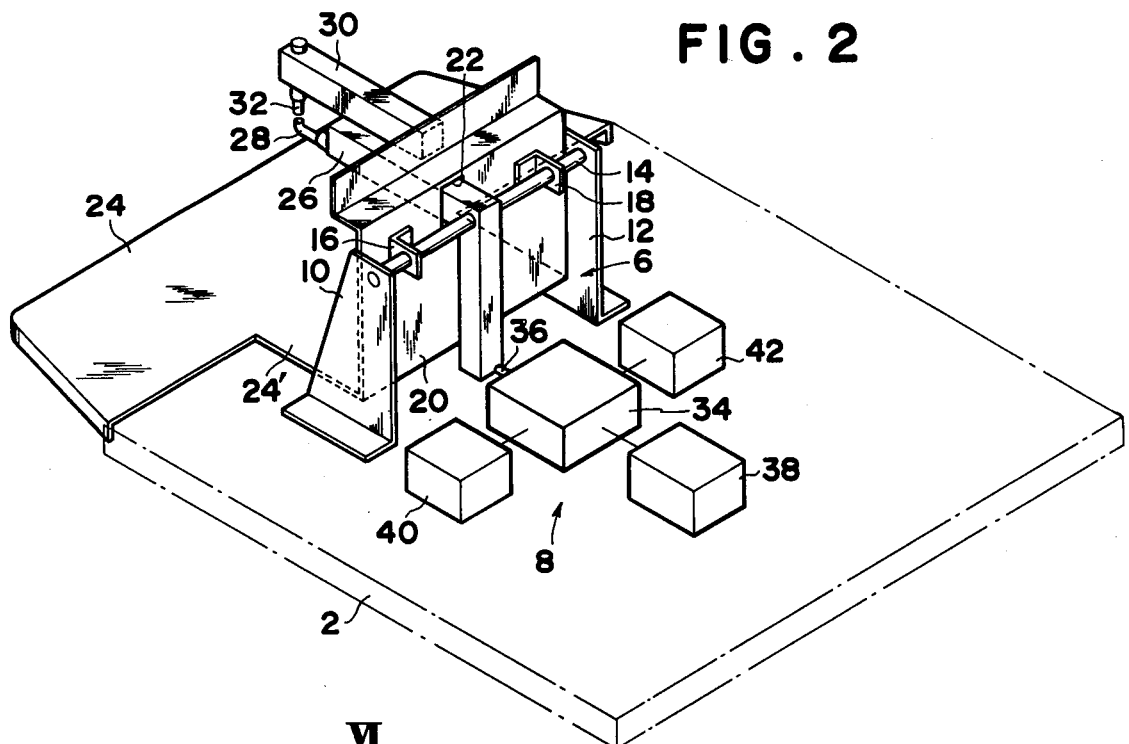
FIG. 2 is a perspective view of an orthodontic welding apparatus embodying the invention and shows a principal mechanism.

Adjacent the switching device 34, there are disposed a charging transformer 38, condenser 40 and discharging transformer 42. An electrical circuit of these elements 34, 38, 40, 42 is shown in FIG. 4.

As shown in FIG. 1, on the front side of the covering 4, there are provided two holes 44 and 46 through which the holders 26 and 30 are extended, a switch 48 and a welding control knob 50. A switch 52 and a knob 54 are electrically connected to a heat treatment device 56 which is positioned at the upper portion of the casing 4. Beside the heat-treatment device 56, a receptacle 58 is positioned in which some materials or articles to be welded are placed. The casing has a cover plate 60 which is hinged at 62 and 64 to cover the heat treatment device 56 and the receptacle 58.

Figure 5:
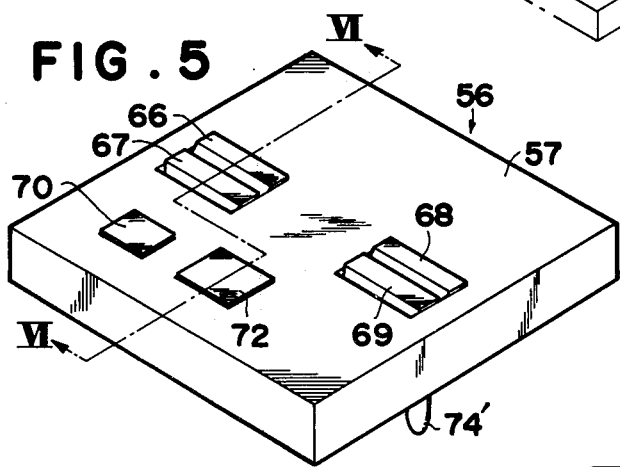
FIG. 5 is a perspective view of an attachment for a heat-treatment.
Figure 6:
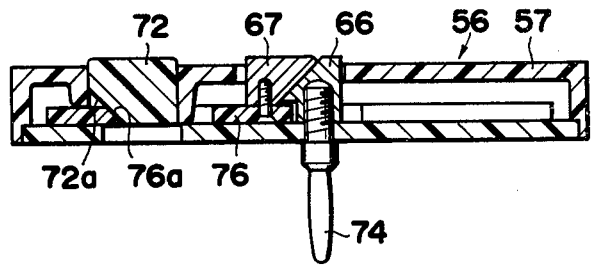
FIG. 6 is a sectioned view of the attachment for a heat-treatment, taken along VI–VI of FIG. 5.

The heat treatment device 56 will be described with reference to FIGS. 5 and 6. A plate-type package 57 contains two pairs of engagement teeth 66, 67, 68, 69, a switch plate 70 and a button 72, all of which are slightly projected through holes above the plane of the package 57. As well shown in FIG. 6, each of the teeth is made of a suitable conductive material and has a connector 74, 74'. The other teeth 67 and 69 are connected a slidable plate 76. The slidable plate 76 has a slant 76a with which a slant portion 72a of the button 72 is contacted such that a downward movement of the button 72 forces to move or slide the slidable plate 76 in the left hand direction of the drawing against a spring (not shown) which urges the slidable plate 76 to abut against the button 72.

An operation of the apparatus will be described with reference, in the first place, to FIGS. 3A, 3B and 4. First of all, the switch 48 is put on so that an Alternating Current is fed to the discharging transformer, and then materials to be welded together are manually inserted in position between the upper electrode 32 and the lower electrode 28. After the materials are positioned accurately between the electrodes 28 and 32, the switching board 24 is pushed or pressed while the materials are kept in position so that the switching board 24 is pivoted downwardly about the bar 14 as shown in FIG. 3B. Successively, the switching board 24 is pushed downward a little bit further, and the lower electrode 28 is oppressed by the upper electrode 32 so that the lower electrode 28 and the holder 26 are pivoted about the bar 14. The pivotal movement of the holder 26 contacts and urges the acuator 36 of the switching device 34 so that the switching device 34 is switched on. When the actuator is urged, the switching device 34 which has been connected to the charging transformer 38, is then connected to the discharging transformer 42, as shown by phantom line 34' (FIG. 4). Then an electric current for welding is fed from the discharging transformer 42 to the upper electrode 32 and the lower electrode 28 to achieve a spot welding.

After a desired welding is finished, the switching board 24 is released to return the upper and lower electrodes to the original position. When the two electrodes are returned, an air space is formed between the two electrodes and the welded materials will be then removed from the position between the two electrodes. When the switching board 24 is released as described, the actuator 34 which was oppressed by the lower portion of the holder 26 is retrieved, and the switching device 34 which was being connected to the discharging transformer 42 during the welding operation is then connected to the charging transformer 38 for the following spot welding operation.

An operation of a heat treatment will be described with reference to FIGS. 5 and 6. A wire or the like (not shown) to be heat-treated is engaged at its one end by the teeth 66 and 67 and at the other end by the teeth 68 and 69, by merely pushing and then releasing the button 72. In other words, when the button is pushed, the teeth 66, 67 on one side and the teeth 68, 69 on the other are opened by means of the sliding movement of the member 76. Then the material to be heat-treated is inserted into the openings formed by the lateral movement of the teeth 67 and 69, and then the button is released to grasp the inserted portion of the wire material. An operation of the switch 52 (FIG. 1) allows an electric current to feed to the teeth 66, 67, 68, 69 through the terminals 74 and 75, thereby allowing a desired heat-treatment.

Though the present invention has been described with reference to preferred embodiment thereof, many modifications and alterations may be made within the spirit of the invention.

What is claimed is:

1. A welding apparatus for dental purposes comprising:
    a pair of supporting members vertically disposed on a base plate,
    a bar fixed at its both ends to the upper portion of said supporting members,
    a plate means which has a vertical extension and is pivotally connected with said bar so that it is pivotable relative to said base plate,
    an upper arm which has an upper electrode at one end thereof and is connected at the other end to the vertical extension of said plate means,
    a lower arm which has a lower electrode at one end thereof and is swingably supported by said bar at the substantially middle portion of said bar so that it is pivotable relative to said base plate,
    a switch means having a microswitch which is switched upon contact by said lower arm, and
    an electrical circuit device which has charging and discharging transformers,
    wherein when said plate means is pushed downward and pivoted relative to said base plate, said upper electrode pushes said lower electrode to thereby pivot said lower arm and actuate said switch means, thereby feeding an electric current to said upper and lower electrodes.

2. The welding apparatus as claimed in claim 1, wherein said lower arm is "L" shape and has a hole at the angled portion thereof, said bar being inserted through said hole of the lower arm thereby to swingably support said lower arm.

3. The welding apparatus as claimed in claim 1, wherein said plate means and the vertical extension thereof are integrally formed of plastic material.

4. The welding apparatus as claimed in claim 2, wherein said plate means has a hole at the vertical extension thereof and two members swingably contacted with said bar, said members being fixed to said vertical extension, said lower arm extending through the hole of said plate member.

5. The welding apparatus as claimed in claim 1 wherein said apparatus further comprises a cover member and a spring, said spring being connected with the top end portion of said plate means and said cover member, thereby lifting said upper electrode upwardly for forming a space between said upper and lower electrodes.

6. The welding apparatus as claimed in claim 5, a spring is connected at its one end with the lower portion of said lower arm and with said casing at the other end.

* * * * *